United States Patent
Spinelli et al.

(10) Patent No.: US 9,340,508 B2
(45) Date of Patent: May 17, 2016

(54) PROCESS FOR THE PREPARATION OF 6-(7-((1-AMINOCYCLOPROPYL)METHOXY)-6-METHOXYQUINOLIN-4-YLOXY)-N-METHYL-1-NAPHTHAMIDE AND SYNTHETIC INTERMEDIATES THEREOF

(71) Applicant: Clovis Oncology Italy S.r.l., Milan (IT)

(72) Inventors: Silvano Spinelli, Milan (IT); Valeria Livi, Milan (IT)

(73) Assignee: CLOVIS ONCOLOGY ITALY S.R.L., Milan (IT)

(*) Notice: Subject to any disclaimer, the term of this patent is extended or adjusted under 35 U.S.C. 154(b) by 0 days.

(21) Appl. No.: 14/661,105

(22) Filed: Mar. 18, 2015

(65) Prior Publication Data

US 2015/0191429 A1    Jul. 9, 2015

Related U.S. Application Data

(62) Division of application No. 14/138,302, filed on Dec. 23, 2013, now Pat. No. 9,012,645, which is a division of application No. 13/256,722, filed as application No. PCT/EP2010/001519 on Mar. 11, 2010, now Pat. No. 8,642,767.

(30) Foreign Application Priority Data

Mar. 16, 2009 (IT) ............... MI2009A0397

(51) Int. Cl.
| | | |
|---|---|---|
| C07D 215/22 | (2006.01) |
| C07C 217/44 | (2006.01) |
| C07C 271/24 | (2006.01) |
| C07C 269/04 | (2006.01) |

(52) U.S. Cl.
CPC ............ *C07D 215/22* (2013.01); *C07C 217/44* (2013.01); *C07C 269/04* (2013.01); *C07C 271/24* (2013.01); C07C 2101/02 (2013.01)

(58) Field of Classification Search
CPC .................................................. C07D 215/22
See application file for complete search history.

(56) References Cited

U.S. PATENT DOCUMENTS

| 8,163,923 B2 * | 4/2012 | Chen ................. C07D 215/233 546/159 |
| 8,642,767 B2 | 2/2014 | Spinelli et al. |
| 9,012,645 B2 | 4/2015 | Spinelli et al. |
| 2008/0227812 A1 | 9/2008 | Chen |
| 2014/0114075 A1 | 4/2014 | Spinelli et al. |

FOREIGN PATENT DOCUMENTS

| EP | 1548008 | | 6/2005 |
| WO | 2008/112408 | * | 9/2008 |
| WO | WO 2008/112408 | | 9/2008 |

OTHER PUBLICATIONS

D'Angelo et al. "Design, Synthesis, and Biological Evaluation of Potent c-Met inhibitors" J. Med. Chem. 2008, v51, pp. 5766-5779.
International Search Report and Written Opinion Issued in International Application No. PCT/EP2010/001519, dated Aug. 6, 2010.
Kim et al. "Generation of Patterned Color Images in Polymer Film with Photogenerated Base" Chem. Lett. 2000, pp. 712-713.
Tois, J. et al., "Novel and convenient synthesis of 4(1H)quinolones," Tetrahedron Letters, Elsevier, Amsterdam, vol. 46, No. 5, Jan. 31, 2005, pp. 735-737, XP004705840, ISSN: 0040-4039.
van Galen et al., "1H-Imidazo[4,5-c]quinolin-4-amines: Novel Non-Xanthine Adenosine Antagonists" J. Med Chem. 1991, v34, pp. 1202-1206.
Welin, Sun et al., "Biosteric Replacement in the Design and Synthesis of Ligands for Nicotinic Acetylcholine Receptors," Medicinal Chemistry Research, Birkauser-Verlag, BO, vol. 14, No. 5, Jul. 1, 2005, pp. 241-259, XP019428169, ISSN: 1554-8120.

* cited by examiner

*Primary Examiner* — D M Seaman
(74) *Attorney, Agent, or Firm* — Swanson & Bratschun, L.L.C.

(57) ABSTRACT

A process for the preparation in high yields and purity of the compound 6-(7-((1-aminocyclopropyl)methoxy)-6-methoxyquinolin-4-yloxy)-N-methyl-1-naphthamide of formula (I) and of the pharmaceutically acceptable salts thereof is described. The process has various advantages over those previously described, in particular it avoids the use of acyl azide intermediates and their Curtius rearrangement. Novel intermediates useful for the preparation of compound (I) are also described.

4 Claims, No Drawings

PROCESS FOR THE PREPARATION OF 6-(7-((1-AMINOCYCLOPROPYL)METHOXY)-6-METHOXYQUINOLIN-4-YLOXY)-N-METHYL-1-NAPHTHAMIDE AND SYNTHETIC INTERMEDIATES THEREOF

This application is a divisional of U.S. application Ser. No. 14/138,302, filed Dec. 23, 2013. U.S. application Ser. No. 14/138,302 is a divisional of U.S. application Ser. No. 13/256,722 filed on Sep. 15, 2011, now U.S. Pat. No. 8,642,767. U.S. application Ser. No. 13/256,722 is a 371 U.S. National phase of PCT/EP2010/001519 filed on Mar. 11, 2010, which claims priority to and benefit of Italian Application No. MI2009A000397 filed on Mar. 16, 2009, all of which are incorporated herein by reference in their entireties.

FIELD OF THE INVENTION

The present invention relates to a process for the preparation of 6-(7-((1-aminocyclopropyl)methoxy)-6-methoxyquinolin-4-yloxy)-N-methyl-1-naphthamide of formula (I) and the pharmaceutically acceptable salts thereof. A further object of the invention are novel intermediates useful for the preparation of compound (I).

TECHNOLOGICAL BACKGROUND

WO 2008/112408 A1 and US 2008/0227812 A1 disclose angiogenesis inhibitors with quinoline structure, useful for the treatment of neoplasias.

One of the disclosed products is 6-(7-((1-aminocyclopropyl)methoxy)-6-methoxyquinolin-4-yloxy)-N-methyl-1-naphthamide of formula (I), described in example 3 of the above mentioned patent applications.

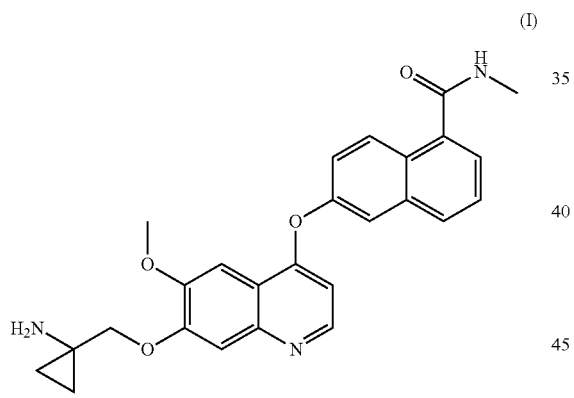

According to said documents, compound (I) is prepared by removing the benzyloxycarbonyl protective group from the compound benzyl 1-((6-methoxy-4-(5-(methylcarbamoyl)-naphthalen-2-yloxy)quinolin-7-yloxy)methyl)cyclopropyl carbamate (II):

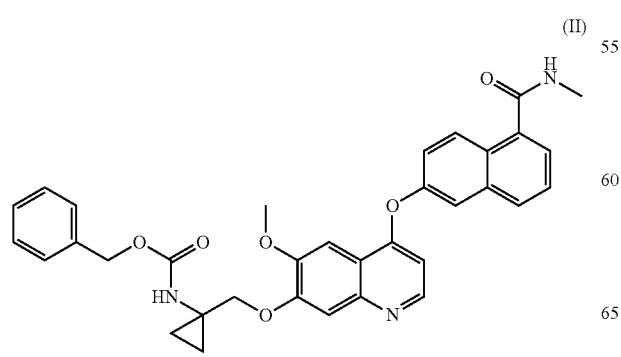

in acid medium or by hydrogenolysis, to give compound (I).

Compound (II) is obtained in a number of steps with different processes in which the benzyloxycarbonyl protected 1-amino-1-cyclopropylmethyl moiety is introduced by subjecting the acyl azide obtained from 1-((6-methoxy-4-(5-(methylcarbamoyl)naphthalen-2-yloxy)quinolin-7-yloxy)methyl)cyclopropanecarboxylic acid of formula (III):

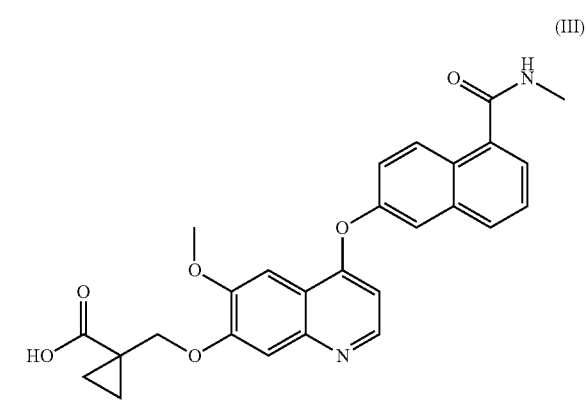 [SMILES: CNC(=O)c1cccc2cc(Oc3ccnc4cc(OCC5(C(=O)O)CC5)c(OC)cc34)ccc12]

to Curtius rearrangement, in the presence of benzyl alcohol, or by alkylation of 6-(7-hydroxy-6-methoxyquinolin-4-yloxy)-N-methyl-1-naphthamide of formula (IV):

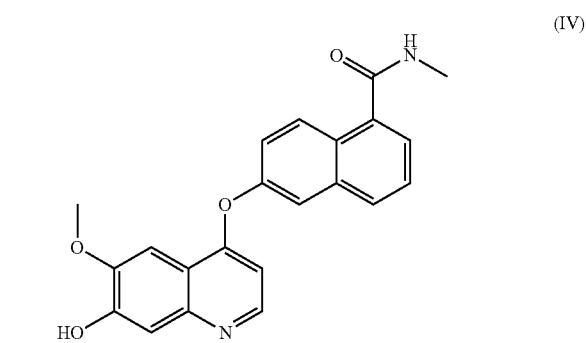 [SMILES: CNC(=O)c1cccc2cc(Oc3ccnc4cc(O)c(OC)cc34)ccc12]

with 1-benzyloxycarbonylamino-1-methylsolfonyloxymethyl-cyclopropane of formula (V):

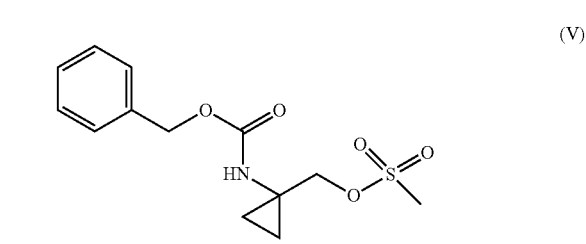 [SMILES: CS(=O)(=O)OCC1(NC(=O)OCc2ccccc2)CC1]

The above mentioned applications do not provide yields concerning both the preparation of compound (II) by the two above mentioned reactions, and the conversion of compound (II) to (I).

Compound (III) is prepared by a process in which the 1-carboxy-1-cyclopropylmethyl moiety is introduced in 4-hydroxy-3-methoxyacetophenone as in the form of the ethyl ester, followed by formation of the 4-hydroxyquinoline ring and, finally, by the introduction of the 1-naphthylcarboxamido fragment.

It is well known that the reactions requiring the use of azides, such as the formation of acyl azides, or Curtius rearrangement of the latter, are potentially hazardous as they involve risk of explosions, therefore they are not suitable for use in preparations on large scale.

The synthetic methods reported in WO 2008/112408 and US 2008/0227812 include, inter alia, a general synthetic scheme in which the cycloalkyl-alkyl portion of the products is introduced by reaction between a cycloalkyl-alkyl mesylate and an hydroxy or amino acetophenone, followed by nitration to give a nitroacetofenone, reduction of the nitro group to amino group, formation of the 4-hydroxyquinoline ring and further work up of the latter to the final products. The above mentioned applications do not provide examples of the use of this process for compound (I) or the other described products.

DISCLOSURE OF THE INVENTION

The present invention relates to a process for the preparation of compound (I) and the pharmaceutically acceptable salts thereof in high yields and purity. The process has various advantages over those described above, in particular it avoids the steps of formation of acyl azide corresponding to the product (III) and its Curtius rearrangement to give the product (II). Furthermore, the invention provides novel intermediates useful for the preparation of compound (I).

An aspect of the invention is a process for the preparation of the compound 6-(7-((1-aminocyclopropyl)methoxy)-6-methoxyquinolin-4-yloxy)-N-methyl-1-naphthamide of formula (I):

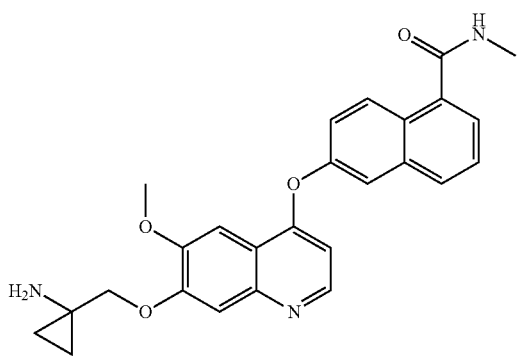

(I)

or a pharmaceutically acceptable salt thereof,
comprising the following steps:
a) reaction of an amino-protected 1-amino-1-hydroxymethylcyclopropane of formula (VI):

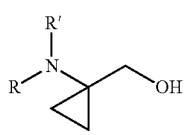

(VI)

in which R and R' taken together with the nitrogen atom they are linked to are a protected primary amino group, with 4-hydroxy-3-methoxyacetofenone of formula (VII):

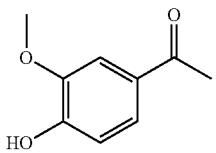

(VII)

under Mitsunobu reaction conditions, to give a compound of formula (VIII):

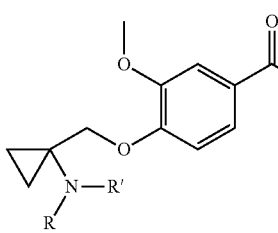

(VIII)

in which R and R' are as defined above;

b) nitration of a compound of formula (VIII) to give a compound of formula (IX):

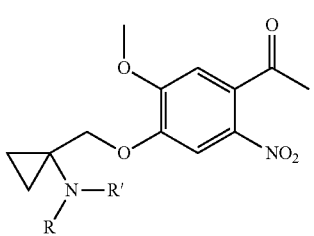

(IX)

in which R and R' are as defined above;

c) reaction of a compound of formula (IX) with a compound of formula (XV):

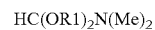

HC(OR1)$_2$N(Me)$_2$ (XV)

in which R1 is a straight or branched $C_1$-$C_6$ alkyl or a $C_3$-$C_6$-cycloalkyl, to give a compound of formula (X):

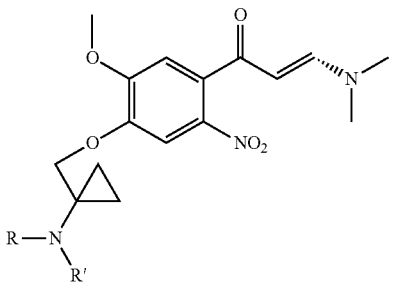

(X)

in which R and R' are as defined above and the line ⁓ means that the double bond of the beta-enaminoketone group can be in cis or trans configuration;

d) reduction of the nitro group of a compound of formula (X) and concomitant cyclization to give a compound of formula (XI) which can be in equilibrium with its tautomeric form (XIa):

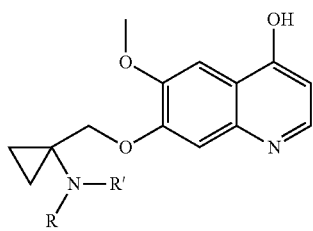

(XI)

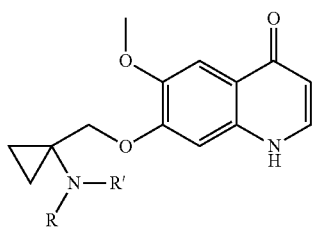

(XIa)

in which R and R' are as defined above;

e) conversion of a compound of formula (XI) or (XIa) to a compound of formula (XII):

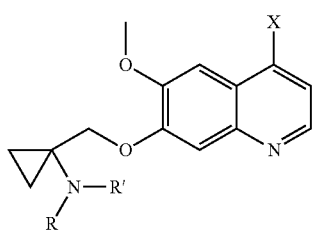

(XII)

in which X is selected from Cl, Br or I and R and R' are as defined above;

f) reaction of a compound of formula (XII) with 6-hydroxy-N-methyl-1-naphthamide of formula (XIII):

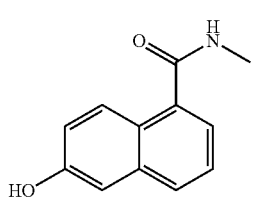

(XIII)

to give a compound of formula (XIV):

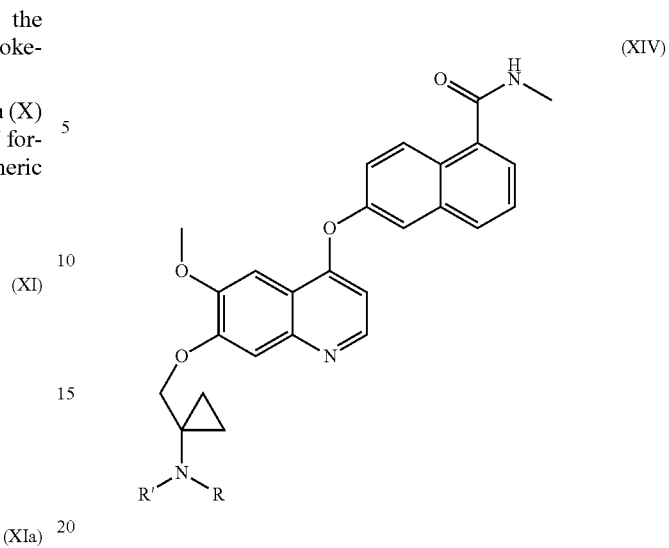

(XIV)

in which R and R' are as defined above;

g) deprotection of the protected primary amino group of compound of formula (XIV) to give compound of formula (I);

h) optional conversion of compound (I) to a pharmaceutically acceptable salt thereof through known methods.

The primary amine function present in the compounds (VI) and (VIII)-(XII) can be protected by using any protective groups known and compatible with the reaction conditions the above mentioned compounds are subjected to. Examples of protective groups that can be advantageously used are those for which in the compounds (VI) and (VIII)-(XII) R' is hydrogen and R is selected from the group consisting of: benzyl optionally substituted at the aromatic ring with up to three substituents selected from the group consisting of halogen, cyano, trifluoromethyl; $C_1$-$C_3$ acyl or $C_7$-$C_{11}$ aroyl such as acetyl and benzoyl; $C_1$-$C_3$ sulfonyl or $C_6$-$C_{10}$ arylsulfonyl such as trifluoromethanesulfonyl, benzene sulfonyl, p-toluenesulfonyl; $C_1$-$C_4$ alkoxycarbonyl such as methoxycarbonyl, ethoxycarbonyl, tert-butoxycarbonyl, allyloxycarbonyl; benzyloxycarbonyl optionally substituted at the aromatic ring with up to three substituents selected from the group consisting of halogen, cyano, trifluoromethyl, such as benzyloxycarbonyl; or R' is a tri ($C_1$-$C_3$ alkyl)silyl derivative and R is $C_1$-$C_4$ alkoxycarbonyl or benzyloxycarbonyl optionally substituted at the aromatic ring with up to three substituents selected from the group consisting of halogen, cyano, trifluoromethyl, to form together with the nitrogen atom they are linked to a N-silylated carbamate such as tert-butyl N-trimethylsilyl carbamate (Tetrahedron Lett., 1997, 38, 191); or R' and R together with the nitrogen atom they are linked to form a phthalimido group.

Compounds (VI) are known or can be prepared with known methods. Some compounds, for example the compound of formula (VI) in which R is benzyloxycarbonyl, are also commercially available (China Gateway).

The reaction between a compound (VI) and 4-hydroxy-3-methoxyacetofenone (VII) to give a compound (VIII) takes place under the conditions commonly used for the Mitsunobu reaction, a well known reaction (Synthesis 1981, 1-28; Org. React. 1992, 42, 335-656) which can be used for the preparation of alkyl aryl ethers under mild conditions. Compounds (VIII) can be prepared using any reagent commonly used in the Mitsunobu reaction between a phenol and an alcohol. The preparation of compounds (VIII) is usually carried out using an equimolar amount or a slight molar excess of a phosphine and an azodicarboxylate or an azodiamide which can be used in the Mitsunobu reaction, with respect to 3-hydroxy-4-methoxyacetofenone and compound (VI).

The latter are usually employed in equimolar ratios or in an excess up to 30% of compound (VI) with respect to 3-hydroxy-4-methoxyacetofenone. The reaction is usually carried out in an organic solvent, such as tetrahydrofuran, dioxane, methylene chloride, or mixtures thereof. Examples of phosphines which can be used are trialkylphosphines, e.g. tributylphosphine and tri-tert-butilphosphine; dialkylarilphosphines, e.g. diethylphenylphosphine; diarilalkylphosphines, e.g. diphenylisopropylphosphine; triarylphosphines, e.g. triphenylphosphine, (4-dimethylaminophenyl)diphenylphosphine and diphenyl(2-pyridyl)phosphine.

Examples of azodicarboxylates are dimethylazodicarboxylate, diethylazodicarboxylate, diisopropylazodicarboxylate and dibenzilazodicarboxylate. Examples of azodiamides are the N,N,N',N'-tetramethylazodicarboxyamide and 1,1'-(azodicarbonyl)dipiperidine. A triarylphosphine, for example triphenylphosphine, is preferably used as the phosphine. Diisopropyl azodicarboxylate is preferably used as the azodicarboxylate. The reaction is preferably carried out in tetrahydrofuran at a temperature between −10° C. and 10° C., preferably at 0° C., first contacting triphenylphosphine and diisopropylazodicarboxylate, then adding 4-hydroxy-3-methoxyacetofenone and finally compound (VI).

The nitration of a compound (VIII) to give a compound (IX) can be performed using the conventional conditions for the nitration of aromatic derivatives. The reaction is usually carried out at a temperature ranging from −5° C. to 5° C., preferably at 0° C., using a mixture of concentrated nitric acid and acetic anhydride as the nitration reagent.

The reaction between a compound (IX) and a compound (XV) to give a compound (X) is usually carried out in an organic solvent selected from toluene, xylene, N,N-dimethylformamide, N,N-dimethylacetamide, N-methylpyrrolidone, or mixtures thereof, using a molar excess of compound (XV) at a temperature ranging from 50° C. to the boiling temperature of the solvent and for a time comprised between 1 hour and 24 hours. Compounds (XV) are known and commercially available. The reaction is preferably carried out in N,N-dimethylformamide for about two hours at a temperature of about 100° C., using 2 molar equivalents of N,N-dimethylformamide dimethyl acetal with respect to compound (IX).

Transformation of a compound (X) into a 4-hydroxyquinoline derivative (XI) or into the tautomeric form of (XI) with 4-quinolone structure (XIa) is carried out by reductive cyclization using a modification of Leimgruber-Batcho reaction, a reaction generally used for the synthesis of indoles (Organic Syntheses, 1985, vol. 63, 314) but also useful for the synthesis of 4-hydroxyquinoline/4-quinolone derivatives, as described in Tetrahedron Letters, 2005, Vol. 46, 735-737. All the procedures and reagents able to reduce an aromatic nitro group to an amino group can be used, such as catalytic hydrogenation; hydrogen transfer hydrogenation, such as ammonium formate in the presence of palladium on charcoal; reductions with metals, e.g. zinc in acetic acid, iron in acetic acid, stannous chloride; sodium dithionite. For the purposes of the invention, powder iron is preferably used as the reducing agent and the reaction is usually carried out at a temperature of 80° C. in the presence of acetic acid as the solvent.

Compounds (XI)/(XIa) are transformed into compounds (XII) through well known reactions for the transformation of 4-hydroxyquinoline/4-quinolone derivatives into 4-alogeno-quinoline derivatives. Reaction conditions which can advantageously be used comprise the use of phosphorous oxyhalide in molar excess such as $POCl_3$ or $POBr_3$ to the compound of formula (XI)/(XIa), optionally in the presence of a solvent such as chloroform or methylene chloride and of an organic tertiary base such as triethylamine or diethylisopropylamine. The reaction is preferably carried out using $POCl_3$ as the reaction solvent and operating at a temperature between about 60° C. and about 100° C., more preferably at about 80° C.

The reaction of a compound (XII) with 6-hydroxy-N-methyl-1-naphthamide (XIII) to give a compound (XIV) can be carried out reacting an equimolar amount or a slight excess of compound (XIII) with respect to compound (XII) in an organic solvent such as ethyl acetate, tetrahydrofuran, dioxane, dimethylformamide, dimethylacetamide, N-methylpyrrolidone, dimethylsulfoxide, pyridine, 2,6-dimethylpyridine, optionally in the presence of an inorganic base such as an alkali or alkaline-earth metal hydroxide or an alkali metal carbonate or bicarbonate, or in the presence of an organic base such as triethylamine, diisopropylethylamine, pyridine or 4-dimethylaminopyridine. The reaction is usually carried out in dioxane or 2,6-dimethylpyridine at a reflux temperature, in the presence of a 10-20% molar excess of compound (XIII) with respect to compound (XII), operating in the presence of a 5% molar excess of 4-dimethylaminopyridine with respect to compound (XII).

Compound (XIII) is known and can be prepared according to known methods, such as that disclosed in WO 2008/112408.

The reaction of a compound (XIV) to give compound (I) consists in the removal of the primary amino group protective group from a compound (XIV), using specific, well known methods, depending on the protective group present. For example, when R' is hydrogen and the R group is methoxycarbonyl, ethoxycarbonyl, tert-butoxycarbonyl, benzyloxycarbonyl, hydrolysis in acid medium is preferably used, such as treatment of compound (XIV) with an inorganic acid such as hydrochloric or hydrobromic acid or, for the tert-butoxycarbonyl group, treatment with an organic acid such as trifluoroacetic acid. The benzyloxycarbonyl group can also be removed under hydrogenolysis conditions, by catalytic hydrogenation or by hydrogen transfer hydrogenation. The benzyloxycarbonyl group is preferably removed in acidic conditions with hydrobromic acid in acetic acid, operating at a temperature ranging from about 20° C. to about 50° C., preferably at about 30° C.

Compound (I) can optionally be converted to a pharmaceutically acceptable salt thereof through conventional methods.

A further aspect of the invention is a process for the preparation of the compound 6-(7-((1-aminocyclopropyl)methoxy)-6-methoxyquinolin-4-yloxy)-N-methyl-1-naphthamide of formula (I) or of a pharmaceutically acceptable salt thereof, comprising the following steps:

i) reaction between a compound of formula (VI):

in which R and R' taken together with the nitrogen atom they are linked to are a protected primary amino group, with a compound of formula (XVI):

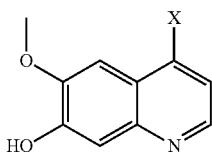

(XVI)

in which X is selected from Cl, Br or I, under the Mitsunobu reaction conditions, to give a compound of formula (XII):

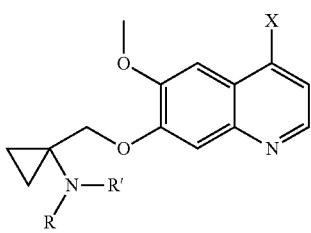

(XII)

in which X, R and R' are as defined above, followed by
ii) transformation of compound of formula (XII) into compound of formula (I) through known methods.

The Mitsunobu reaction between a compound (VI) and a compound (XVI) can be carried out under the conditions described above for the reaction between a compound (VI) and 4-hydroxy-3-methoxyacetofenone (VII). A compound (XVI) in which X is Cl or Br is preferably used.

Compounds (XVI) can be prepared with known methods. For example, compound (XVI) in which X is Cl can be prepared according to what described in J. Med. Chem. 2008, 51, 5766-5779. Compound (XVI) in which X is Cl is also commercially available.

Compounds (VIII), (IX), (X), (XI) and (XII) are novel and are a further aspect of the invention.

A further aspect of the invention is the use of compounds of formula (VIII), (IX), (X), (XI) or (XII) in a process for the preparation of compound (I) or of the pharmaceutically acceptable salts thereof.

The use of the Mitsunobu reaction for the preparation of compounds (VIII) has advantages over the alkylation of compound VII with the mesylate obtained from compound (VI) disclosed in WO 2008/112408 A2 and in US 2008/0227812, such as milder reaction conditions (e.g. lower reaction temperatures and reduced reaction times), improved yields, easiness of purification and purity profile of the obtained intermediate (VIII). In addition, the use of the Mitsunobu reaction between compound (VI) and compound (XVI) for the preparation of compounds (XII) provides an easy entry to the latter compound, which is overall more convenient than the multi-step process disclosed in the above mentioned patent applications starting from the mesylate obtained from compound (VI).

The invention will be illustrated by the following examples.

EXAMPLES

The abbreviations reported in the following are used in the examples. All of the other abbreviations are conventional representations of chemical formulae.

ACN: acetonitrile, AcOH: acetic acid, Ac$_2$O: acetic anhydride, DEAD: diethyl azodicarboxylate, DIAD: diisopropyl azodicarboxylate, DIPEA: diisopropylethylamine, DCM: dichloromethane, DMF: N,N-dimethylformamide, DMAP: 4-dimethylaminopyridine, DMSO: dimethylsulfoxide, AcOEt: ethyl acetate, EtOH: ethanol, MeOH: methanol, THF: tetrahydrofuran, TEA: triethylamine, TFA: trifluoroacetic acid.

1H NMR spectra were recorded in the indicated solvent, using a Bruker AVIII500 spectrometer (Software: TOPSPIN VERSION 2.1; Probe: 5 mm PABBO BB-1H/D Z-GRD) or a Varian Mercuryplus300 spectrometer (Software: Vnmr6.1C; Probe: ID_PFG), operating, respectively, at 500 MHz and 300 MHz. The following abbreviations were used: s, singlet; d, doublet; m, multiplet.

LC-spectra MS were recorded in the following conditions:
instrumentation: Agilent 1200&6110MS, ELSD Varian 380-LC.
column: Waters Sunfire C-18 50 mm×4.6 mm, 3.5 µm, termosthatized at 40° C.
mobile phase A: 0.05% TFA in water.
mobile phase B: 0.05% TFA in ACN.
Gradient:

| Time (min) | 0.1 | 1.70 | 2.60 | 2.70 |
|---|---|---|---|---|
| % B | 1 | 99 | 99 | 1 |

Flow: 3.0 mL/min.
Detector: UV @ 214 nm/bw 4 nm
UV @ 254 nm/bw 4 nm
MS
ELSD
Injection: 1 µl.
Analysis time: 2.7 min.

Example 1

Preparation of 1-[(4-acetyl-2-methoxyphenoxy)methyl]-N-benzyloxycarbonyl-1-aminocyclopropane

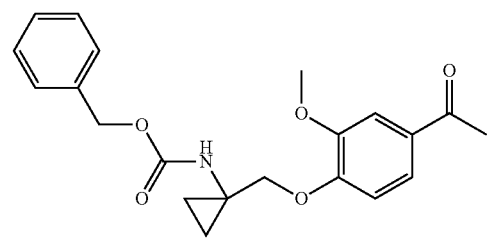 [SMILES: COc1cc(C(C)=O)ccc1OCC1(NC(=O)OCc2ccccc2)CC1]

A 10 L reactor equipped with mechanical stirrer was loaded with triphenylphosphine (340.0 g, 1.296 mol) and THF (2 L) and the suspension was cooled with an ice bath. The stirred suspension was then slowly added with DIAD (264 g, 1.296 mol) over 30 minutes. After stirring for 30 min at 0° C., the stirred suspension was added dropwise with a solution of 4-hydroxy-3-methoxyacetofenone (180 g, 1.08 mol) and DIPEA (210 g, 1.62 mol) in THF (1500 mL). The suspension was left under stirring for 45 min at 0° C., then added dropwise with a solution of 1-benzyloxycarbonylamino-1-hydroxymethylcyclopropane (China Gateway) (240 g, 1.08 mol) in THF (1500 mL). After 1 h, LC-MS analysis of a sample from the reaction mixture showed the complete disappearance of 1-benzyloxycarbonylamino-1-hydroxymethylcyclopropane. The reaction mixture was evaporated and the crude product was recrystallized with EtOH 95% (4000 mL) to give 1-[(4-acetyl-2-methoxyphenoxy)methyl]-N-benzyloxycarbonyl-1-aminocyclopropane (214 g, yield: 53.5%) as a white solid.

$^1$H-NMR (300 MHz, CDCl$_3$): δ: 7.41-7.45 (m, 2H), 7.26 (s, 5H), 6.77 (d, 1H), 5.43 (s, 1H), 5.00 (s, 2H), 4.04 (s, 2H), 3.82 (s, 3H), 2.49 (s, 3H), 0.92 (m, 4H).

LC-MS: M+H$^+$: 370.4

The following compounds were prepared analogously:
1-[(4-Acetyl-2-methoxyphenoxy)methyl]-N-ethoxycarbonyl-1-aminocyclopropane;
1-[(4-Acetyl-2-methoxyphenoxy)methyl]-N-tert-butoxycarbonyl-1-aminocyclopropane.

Example 2

Preparation of 1-[(4-acetyl-2-methoxy-5-nitrophenoxy)methyl]-N-benzyloxycarbonyl-1-aminocyclopropane

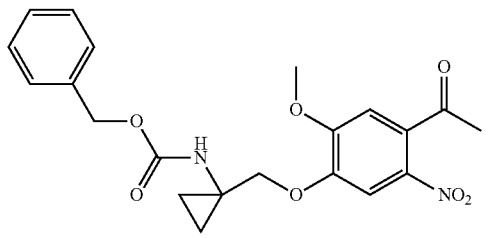 [SMILES: COc1cc(C(C)=O)c([N+](=O)[O-])cc1OCC1(NC(=O)OCc2ccccc2)CC1]

A solution of HNO$_3$ (65%, 3 mL) in Ac$_2$O (2 mL) at 0° C. was slowly added with a suspension of the compound of Example 1 (1.1 g, 2.9 mmol) in Ac$_2$O (3 mL). After stirring at 0° C. for 2 h, the reaction mixture was poured into 50 mL of ice/water and the precipitate was recovered by filtration. The resulting yellow solid was recrystallized with 95% EtOH (5 mL) to give 1-[(4-acetyl-2-methoxy-5-nitrophenoxy)methyl]-N-benzyloxycarbonyl-1-aminocyclopropane (0.69 g, yield: 56%) as a yellow solid.

$^1$H-NMR (300 MHz, CDCl$_3$): δ: 7.52 (s, 1H), 7.26 (s, 5H), 6.67 (s, 1H), 5.36 (s, 1H), 5.02 (s, 2H), 4.05 (s, 2H), 3.86 (s, 3H), 2.42 (s, 3H), 0.94 (m, 4H).

LC-MS: M+H$^+$: 414.41

The following compounds were prepared analogously:
1-[(4-Acetyl-2-methoxy-5-nitrophenoxy)methyl]-N-ethoxycarbonyl)-1-aminocyclopropane;
1-[(4-Acetyl-2-methoxy-5-nitrophenoxy)methyl]-N-(tert-butoxycarbonyl)-1-aminocyclopropane.

Example 3

Preparation of 1-[(4-(3-dimethylaminopropenoyl)-2-methoxy-5-nitrophenoxy)methyl]-N-benzyloxycarbonyl-1-aminocyclopropane

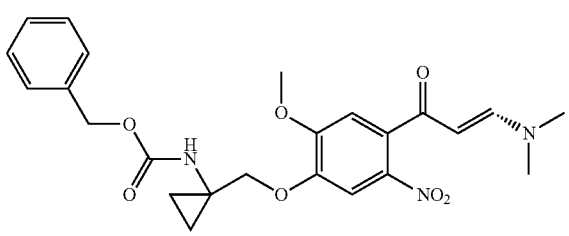

A mixture of the compound of Example 2 (1.7 g, 4.1 mmol) and N,N-dimethylformamide dimethylacetal (0.9 g, 8.2 mmol) in DMF (6 mL) was stirred at 100° C. for 2 h. After cooling at room temperature, the reaction mixture was diluted with water (30 mL) and extracted with AcOEt (3×50 mL). The combined organic phases were washed with brine (2×50 mL), dried and evaporated to give 1-[(4-(3-dimethylaminopropenoyl)-2-methoxy-5-nitrophenoxy)methyl]-N-benzyloxycarbonyl-1-aminocyclopropane (1.9 g, yield: 95%) as a yellow solid.

$^1$H-NMR (300 MHz, CDCl$_3$): δ: 7.50 (s, 1H), 7.27 (s, 5H), 6.75 (s, 1H), 5.44 (s, 1H), 5.23 (s, 1H), 5.11 (br, 1H), 5.01 (s, 2H), 4.04 (s, 2H), 3.83 (s, 3H), 2.78-3.00 (m, 6H), 0.94 (m, 4H)

LC-MS: M+H$^+$: 470.49

The following compounds were prepared analogously:
1-[(4-(3-Dimethylaminopropenoyl)-2-methoxy-5-nitrophenoxy)methyl]-N-ethoxycarbonyl-1-aminocyclopropane;
1-[(4-(3-Dimethylaminopropenoyl)-2-methoxy-5-nitrophenoxy)methyl]-N-tert-butoxycarbonyl-1-aminocyclopropane.

Example 4

Preparation of 1-[(4-hydroxy-6-methoxyquinolin-7-yloxy)methyl]-N-benzyloxycarbonyl-1-aminocyclopropane

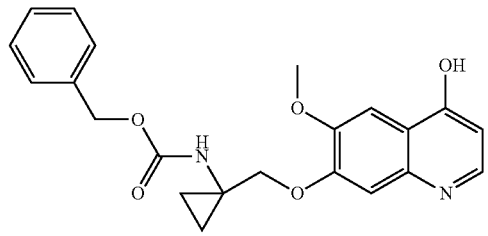

A mixture of the compound of Example 3 (1.5 g, 3.2 mmol) and powder iron (1.8 g, 32 mmol) in AcOH (15 mL) was stirred a 80° C. for 2 h. The reaction mixture was cooled at room temperature, diluted with AcOEt (150 mL), filtered and washed with 50 ml of AcOEt. The filtration liquors were combined, washed with water (2×100 mL) and an NaHCO$_3$ saturated solution (2×100 mL), dried and evaporated to give 1-[(4-hydroxy-6-methoxyquinolin-7-yloxy)methyl]-N-benzyloxycarbonyl-1-aminocyclopropane (1.2 g, yield: 95%) as a yellow solid.

$^1$H-NMR (300 MHz, MeOD): δ: 7.75 (d, 1H), 7.51 (s, 1H), 7.15 (m, 5H), 6.80 (br, 1H), 6.20 (d, 1H), 4.97 (s, 2H), 4.05 (s, 2H), 3.84 (s, 3H), 0.87 (m, 4H).

LC-MS: M+H$^+$: 395.2

The following compounds were prepared analogously:
1-[(4-Hydroxy-6-methoxyquinolin-7-yloxy)methyl]-N-ethoxycarbonyl-1-aminocyclopropane;
1-[(4-Hydroxy-6-methoxyquinolin-7-yloxy)methyl]-N-tert-butoxycarbonyl-1-aminocyclopropane.

Example 5

Preparation of 1-[(4-chloro-6-methoxyquinolin-7-yloxy)methyl]-N-benzyloxycarbonyl-1-aminocyclopropane

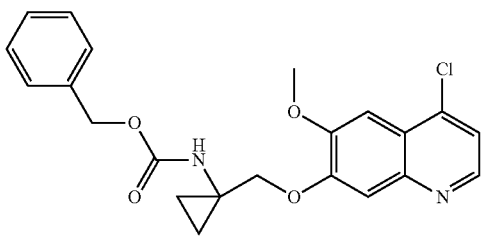 [SMILES: COc1cc2c(Cl)ccnc2cc1OCC1(NC(=O)OCc2ccccc2)CC1]

a) By Chlorination of the Compound of Example 4

A 50 ml round-bottom flask fitted with magnetic stirrer, thermometer, condenser and kept under nitrogen atmosphere, was loaded at 20°/25° C. with 3.90 g (9.89 mmol) of the compound of Example 4 and 25 ml of $POCl_3$. The resulting suspension became a solution after stirring for a few minutes. The solution was heated at 85° C. inner T and after 30 minutes the reaction was monitored by TLC, showing the disappearance of the starting product. The solution was cooled and dropwise added, over about 30 minutes and keeping the temperature below 10° C., to a mixture of 250 ml of DCM and 250 ml of water, cooled at 0° C. After completion of the addition, stirring was maintained for 30 minutes at 0°-10° C. The phases were separated and the aqueous phase was washed with 150 ml of DCM; the phases were separated and the organic phases combined. The combined organic phase was added with 150 ml of water, stirred at 20°/25° C. for 15 minutes and pH was adjusted to 7-8 with a sodium bicarbonate saturated solution. The phases were separated and the organic phase was washed with 150 ml of water; the phases were separated, the organic phase was dried with sodium sulfate, filtered and the solvent evaporated off by distillation under vacuum. Stripping with ethyl ether afforded 3.8 g of a brownish solid. The solid residue was dissolved in 20 ml of tert-butyl methyl ether, stirring at 20°/25° C. for an hour; filtered and washed with tert-butyl methyl ether, then dried to obtain 1-[(4-chloro-6-methoxyquinolin-7-yloxy)methyl]-N-benzyloxycarbonyl-1-aminocyclopropane (3.4 g; yield: 87%) having ($^1$H-NMR) titre of 95%.

$^1$H-NMR (500 MHz, DMSO-$d_6$) δ ppm: 8.61 (d, 1H), 7.91 (s, 1H), 7.56 (s, 1H), 7.44 (s, 1H), 7.38 (s, 1H), 7.29 (m, 5H), 4.99 (s, 2H), 4.23 (s, 2H), 3.97 (s, 3H), 0.87 (m, 4H).

b) by Mitsunobu reaction between 4-chloro-7-hydroxy-6-methoxyquinoline and 1-benzyloxycarbonylamino-1-hydroxymethylcyclopropane 20 ml of DCM were added with 4-chloro-7-hydroxy-6-methoxyquinoline (300 mg, 1.43 mmol; from China Gateway), 1-benzyloxycarbonylamino-1-hydroxymethylcyclopropane (412 mg, 1.87 mmol, 1.3 eq; from China Gateway) and triphenylphosphine (490 mg, 1.87 mmol, 1.3 eq). The resulting solution was dropwise added with a solution of DEAD (378 mg, 1.87 mmol, 1.3 eq) in 3 ml of DCM, keeping the temperature at 0° C. for 2 hours. The mixture was then left at 10° C. for 20 hours, then filtered to recover the unreacted 4-chloro-7-hydroxy-6-methoxyquinoline. The filtrate was evaporated under vacuum and the resulting residue was added with 20 ml of 95% EtOH and left under stirring for 30 min. The solid was collected by filtration, washed with 5 ml of 95% EtOH and dried under vacuum to give 1-[(4-chloro-6-methoxyquinolin-7-yloxy)methyl]-N-benzyloxycarbonyl-1-aminocyclopropane (273 mg; yield: 46%).

LC-MS: M+H$^+$: 413.1

The following compounds were prepared analogously:

1-[(4-Chloro-6-methoxyquinolin-7-yloxy)methyl]-N-ethoxycarbonyl-1-aminocyclopropane;

1-[(4-Chloro-6-methoxyquinolin-7-yloxy)methyl]-N-tert-butoxycarbonyl-1-aminocyclopropane.

Example 6

Preparation of benzyl 1-[(6-methoxy-4-(5-(methylcarbamoyl)naphthalen-2-yloxy)quinolin-7-yloxy)methyl)]cyclopropyl carbamate (II)

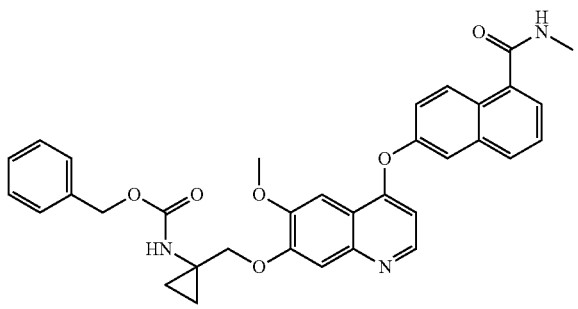 [SMILES: CNC(=O)c1cccc2cc(Oc3ccnc4cc(OCC5(NC(=O)OCc6ccccc6)CC5)c(OC)cc34)ccc12]

A solution of 0.51 g (2.53 mmol) of 6-hydroxy-N-methyl-1-naphthamide prepared according to WO2008/112408, 2, 7 ml of 2,6-lutidine and 0.3 g (2.42 mmol) of DMAP, kept at 20°/25° C. and under nitrogen atmosphere, was added with the compound of Example 5 (1.0 g, NMR titre 95%, 2.30 mmol). The suspension was heated to 140° C. inner temperature for 6 hours; then cooled to 20°/25° C. and added with 80 ml of water and kept under stirring a 20°/25° C. for 1 hour; the suspension was filtered and washed with water, to afford 0.88 g (yield: 66%) of benzyl 1-[(6-methoxy-4-(5-(methylcarbamoyl)naphthalen-2-yloxy)quinolin-7-yloxy)methyl)]cyclopropyl carbamate (II).

$^1$H-NMR (500 MHz, DMSO-$d_6$) δ ppm: δ: 8.56 (d, 1H), 8.50 (d, 1H), 8.39 (d, 1H), 8.04 (d, 1H), 7.94 (s, 1H), 7.87 (s, 1H), 7.59 (m, 4H), 7.41 (s, 1H), 7.44 (s, 1H), 7.30 (m, 5H), 6.56 (d, 1H), 5.01 (s, 2H), 4.48 (s, 2H), 4.23 (s, 2H), 3.95 (s, 3H), 0.87 (m, 4H).

LC-MS: M+H$^+$: 578.3

The following compounds were prepared analogously:

Ethyl 1-[(6-methoxy-4-(5-(methylcarbamoyl)naphthalen-2-yloxy)quinolin-7-yloxy)methyl)]cyclopropyl carbamate;

tert-Butyl 1-[(6-methoxy-4-(5-(methylcarbamoyl)naphthalen-2-yloxy)-quinolin-7-yloxy)methyl)]cyclopropyl carbamate.

Example 7

Preparation of 6-(7-((1-aminocyclopropyl)methoxy)-6-methoxyquinolin-4-yloxy)-N-methyl-1-naphthamide (I)

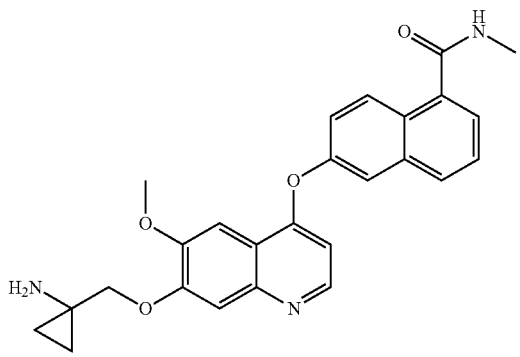 [SMILES: CNC(=O)c1cccc2cc(Oc3ccnc4cc(OCC5(N)CC5)c(OC)cc34)ccc12]

A mixture of the compound of Example 6 (0.24 g, 0.42 mmol) in 2 ml of a solution of 40% HBr in acetic acid was stirred at 30° C. for 3 h, then added with 10 ml of water and the reaction mixture was extracted with AcOEt (2×10 mL). The organic phases were removed. The aqueous solution was dropwise added with a solution of 50% NaOH to reach pH 10. The mixture was extracted with DCM (3×20 mL) and the combined organic phases were dried and evaporated to give a crude containing 6-(7-((1-aminocyclopropyl)methoxy)-6-methoxyquinolin-4-yloxy)-N-methyl-1-naphthamide (I) with purity higher than >94% by LC-MS analysis. This crude was further purified by chromatography on a silica gel column eluting with DCM/MeOH 10:1), to afford 6-(7-((1-aminocyclopropyl)methoxy)-6-methoxyquinolin-4-yloxy)-N-methyl-1-naphthamide (I) having purity higher than 98% by LC-MS analysis (140 mg, yield: 76%).

$^1$H-NMR (500 MHz, DMSO-d$_6$) δ ppm: 8.47 (d, 2H), 7.87 (d, 1H), 7.53 (m, 3H), 7.51 (m, 1H), 7.44 (d, 1H), 7.38 (s, 1H), 6.50 (d, 1H), 6.16 (d, 1H), 5.01 (s, 2H), 4.05 (s, 2H), 4.03 (s, 3H), 3.12 (d, 3H), 2.09 (m, 2H), 0.80 (m, 4H).

LC-MS: M+H$^+$: 444.0

The invention claimed is:

1. A compound of formula (XI) or (XIa):

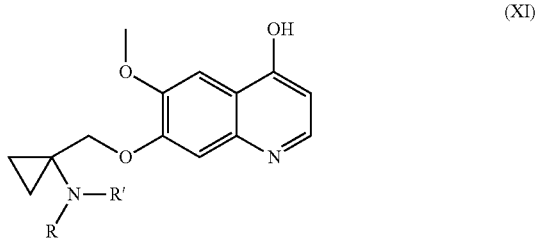

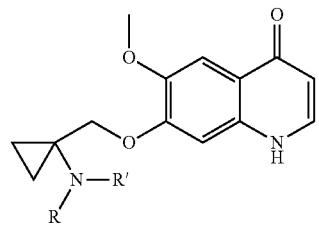

wherein R' is hydrogen and R is selected from benzyl, acetyl, benzoyl, trifluoromethanesulfonyl, benzenesulfonyl, p-toluenesulfonyl, methoxycarbonyl, ethoxycarbonyl, tert-butoxycarbonyl, allyloxycarbonyl and benzyloxycarbonyl optionally substituted on the aromatic ring with up to three substituents selected from halogen, cyano and trifluoromethyl; or R' is trimethylsilyl and R is tert-butoxycarbonyl; or R and R' taken together with the nitrogen atom they are linked to form a phthalimido group.

2. A compound of formula (XII):

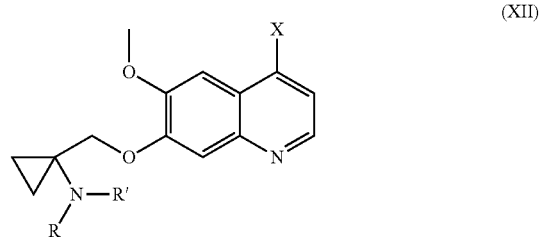

wherein X is selected from the group consisting of Cl, Br and I; wherein R' is hydrogen and R is selected from benzyl, acetyl, benzoyl, trifluoromethanesulfonyl, benzenesulfonyl, p-toluenesulfonyl, methoxycarbonyl, ethoxycarbonyl, tert-butoxycarbonyl, allyloxycarbonyl and benzyloxycarbonyl optionally substituted on the aromatic ring with up to three substituents selected from halogen, cyano and trifluoromethyl; or R' is trimethylsilyl and R is tert-butoxycarbonyl; or R and R' taken together with the nitrogen atom they are linked to form a phthalimido group.

3. A compound as claimed in claim 1, wherein the compound is 1-[(4-Hydroxy-6-methoxyquinolin-7-yloxy)methyl]-N-benzyloxycarbonyl-1-aminocyclopropane.

4. A compound as claimed in claim 2, wherein the compound is 1-[(4-Chloro-6-methoxyquinolin-7-yloxy)methyl]-N-benzyloxycarbonyl-1-aminocyclopropane.

* * * * *